(12) United States Patent
Sengupta et al.

(10) Patent No.: US 8,398,918 B2
(45) Date of Patent: Mar. 19, 2013

(54) SYSTEM AND METHOD FOR CHEMICAL AND BIOLOGICAL AGENT DECONTAMINATION

(75) Inventors: Louise C. Sengupta, Ellicott City, MD (US); Idan Mandelbaum, Columbia, MD (US); Yeshayahu Shyke Goldstein, Gaithersburg, MD (US); Tadd Kippany, Mt. Airy, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 382 days.

(21) Appl. No.: 12/651,220

(22) Filed: Dec. 31, 2009

(65) Prior Publication Data

US 2012/0107173 A1 May 3, 2012

(51) Int. Cl.
*A61L 2/10* (2006.01)
(52) U.S. Cl. .......................................... 422/24; 422/22

(58) Field of Classification Search .................... 422/24, 422/28, 186.3
See application file for complete search history.

(56) References Cited

U.S. PATENT DOCUMENTS 6,593,582 B2 * 7/2003 Lee et al. ................... 250/458.1
6,692,694 B1 * 2/2004 Curry et al. ..................... 422/28

* cited by examiner

*Primary Examiner* — Sean E Conley
(74) *Attorney, Agent, or Firm* — Rossi, Kimms & McDowell

(57) ABSTRACT

A system and method for decontamination of chemical and biological agents over terrain in an outdoor environment is provided that utilizes ultraviolet radiation to break up hydrogen peroxide into radical species that interact with chemical and biological agents to render them harmless. In a preferred embodiment, peroxide is dispersed in a contaminated area and the peroxide is then exposed to ultraviolet radiation that causes the peroxide to dissociate into radical species. The interaction of the radical species formed by the peroxide dissociation with the chemical and biological agents renders them useless.

18 Claims, 3 Drawing Sheets

SYSTEM AND METHOD FOR CHEMICAL AND BIOLOGICAL AGENT DECONTAMINATION

BACKGROUND OF THE INVENTION

The present invention relates to a system and method for chemical and biological agent decontamination. Specifically, the present invention provides a system and method for decontamination of chemical and biological agents over terrain in an outdoor environment.

Conventional techniques of dealing with chemical and biological agents have focused on trying to protect individuals from coming into contact with such agents, for example, through the use of sealed environments equipped with air filtration systems and protective suits. While such measures provide some degree of protection, the effectiveness of such protective measures is limited in situations in which advance notice of potential contamination threat is not readily available. This is particularly true in cases in which individuals may be suddenly exposed in open terrain to airborne chemical and/or biological agents with little advance notice, thereby preventing the individuals from reaching a safe sealed environment or from putting on a protective suit even if one is available. Further, even if one is able to protect oneself from the initial exposure, there is still a problem of decontaminating the surrounding environment, which is often a difficult task when encumbered by protective suits.

Accordingly, it would be desirable to provide a system and method for decontamination of the chemical and biological agents prior to any significant exposure of the agent to individuals or contamination of the environment.

SUMMARY OF THE INVENTION

The present invention provides a system and method for decontamination of chemical and biological agents over terrain in an outdoor environment. The system and method utilize ultraviolet radiation to break up hydrogen peroxide into radical species that interact with chemical and biological agents to render them harmless. In a preferred embodiment, peroxide is dispersed in a contaminated area and the peroxide is then exposed to ultraviolet radiation that causes the peroxide to dissociate into radical species. The interaction of the radical species formed by the peroxide dissociation with the chemical and biological agents renders them useless.

In a preferred embodiment, the generation of ultraviolet radiation includes dispersing explosive submunitions within the agent cloud and detonating the explosive submunitions in a predefined sequence. The explosive submunitions includes four explosive charges totaling approximately 3 kg including two 0.5 kg subunits and two 1.0 kg subunits. The explosives charges are ignited sequentially with a time delay of approximately 500 µs between detonations. The detonation of the explosive submunitions generates ultraviolet flux of approximately 6 J/cm$^2$ at a radius of 5 m. The ultraviolet radiation is in a range of 200-250 nm, and is of sufficient energy to cause the hydrogen peroxide to break up into the radical species in sufficient concentration to passivate or neutralize the agents within the cloud.

The invention further provides a system for decontamination of an agent cloud that includes a mechanism that disperses hydrogen peroxide within the agent cloud, and a mechanism that generates sufficient ultraviolet radiation within the agent cloud to cause at least a portion of the hydrogen peroxide to break up into radical species. In the preferred illustrated embodiment, the mechanism that generates the ultraviolet radiation includes explosive submunitions that are detonated in a predefined sequence. As described above, the submunitions preferably include four explosive charges totaling approximately 3 kg with two 0.5 kg subunits and two 1.0 kg subunits, and are ignited sequentially with a time delay of approximately 500 µs between detonations. The detonation of the explosive submunitions generates ultraviolet flux of approximately 6 J/cm$^2$ at a radius of 5 m, wherein the ultraviolet radiation is in a range of 200-250 nm and is sufficient to cause the hydrogen peroxide to break down into the radical species in sufficient concentration to neutralize the agents within the cloud.

Other features, advantages, embodiments and objectives of the invention will become apparent to one of ordinary skill in the art from the following detailed description of the preferred embodiments of the invention and the accompanying drawings.

BRIEF DESCRIPTION OF THE DRAWINGS

The invention will be described with reference to certain preferred embodiments thereof and the accompanying drawings, wherein.

DETAILED DESCRIPTION OF THE PREFERRED EMBODIMENTS

Figure 1:
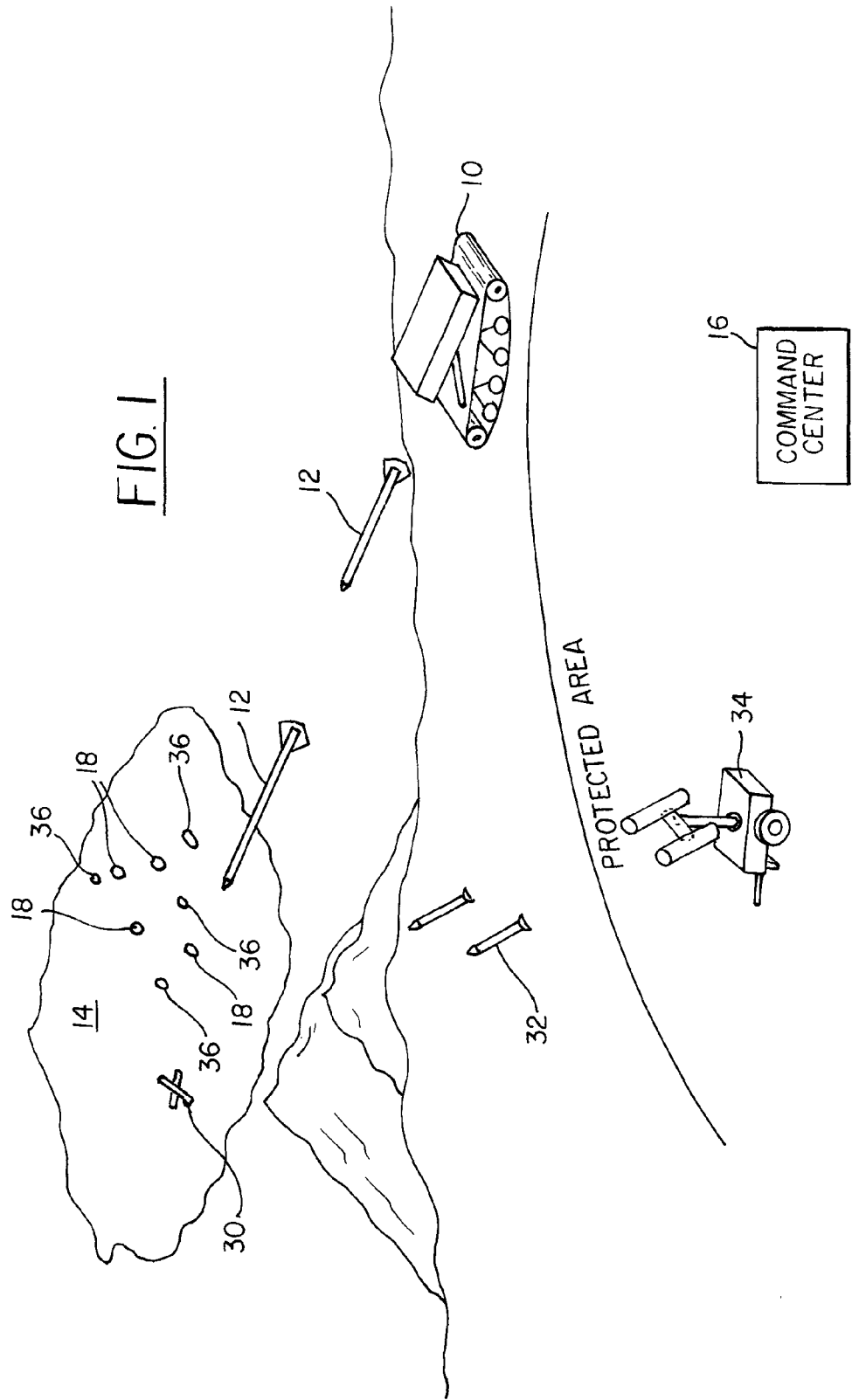
FIG. 1 is a schematic diagram illustrating a system for decontamination of an agent cloud in accordance with an embodiment of the invention.

The present invention provides a system and method for decontamination of chemical and biological agents over terrain in an outdoor environment. The system and method utilize ultraviolet radiation to break up hydrogen peroxide into radical species that interact with chemical and/or biological agents to render them harmless or neutralized. Specifically, in one preferred embodiment, vaporized hydrogen peroxide is dispersed throughout a cloud of chemical and/or biological agent through the use of submunitions delivered by a rocket. Explosive submunitions are also dispersed through the agent cloud along with the vaporized hydrogen peroxide. The explosive submunitions are detonated sequentially to generate shock waves causing compression, which in turn generates heat that causes ultraviolet radiation to be emitted. Radiation in the 200-250 nm range is generated to break up the hydrogen peroxide into OH radicals that attack the chemical as well as biological agents within the cloud and render them useless. The entire process from initial dispersion to detonation is accomplished in a manner of seconds or minutes depending on the particular threat scenario.

While vaporized hydrogen peroxide has been shown effective against both biological and chemical threat agents, this has not been the case within a timeframe required to defeat a rapidly evolving threat such as a cloud of agent dispersed from a missile detonation. Further, although ultraviolet radiation is extremely effective in remediating biological agents, the neutralization of chemical agents by ultraviolet radiation alone requires extremely high ultraviolet energy and gives rather poor kill rates. However, when these methods are combined as in the present system, the ultraviolet radiation splits the hydrogen peroxide into two OH radicals, which have been shown to be the most effective method used to remediate chemical and biological agents in the fastest time, namely, on the order of sub-seconds. Further, depending on the threat agent, any one of the decontamination mechanisms present in the system (i.e. ultraviolet radiation, OH radicals, heat, and OOH⁻ (peroxy anion)) may provide the dominant kill mechanism. Thus, the present system provides a high confidence level that any chemical and/or biological threat will be neutralized regardless of the specific type of agent employed.

A preferred embodiment of the invention will now be described in greater detail with reference to FIG. 1. The system as implemented in FIG. 1 utilizes a conventional mobile launch platform 10 to launch a succession of missiles or rockets 12 into a cloud 14 of chemical and/or biological agent under the control of a command center 16. The rockets 12 contain hydrogen peroxide submunitions and explosive submunitions that are dispersed throughout the cloud 14. The hydrogen peroxide submunitions preferably take the form of canisters having dispersion nozzles that vaporize the hydrogen peroxide contained therein. Once separated from the rockets 12, the dispersion nozzles on the canisters are activated to disperse the hydrogen peroxide in vaporized form throughout the cloud 14 of chemical and/or biological agent. Similarly, the explosive submunitions detonate after separation from the rockets 12 utilizing built-in timers with an appropriate delay in accordance with a predetermined sequence. Ultraviolet radiation is generated from the explosions that is used to breakdown the hydrogen peroxide into the OH radicals. The combination of heat generated by the explosions, the ultraviolet radiation itself, the hydrogen peroxide itself and the OH radicals, all act as countermeasures to neutralize the chemical and/or biological agents contained within the cloud 14.

Figure 2:
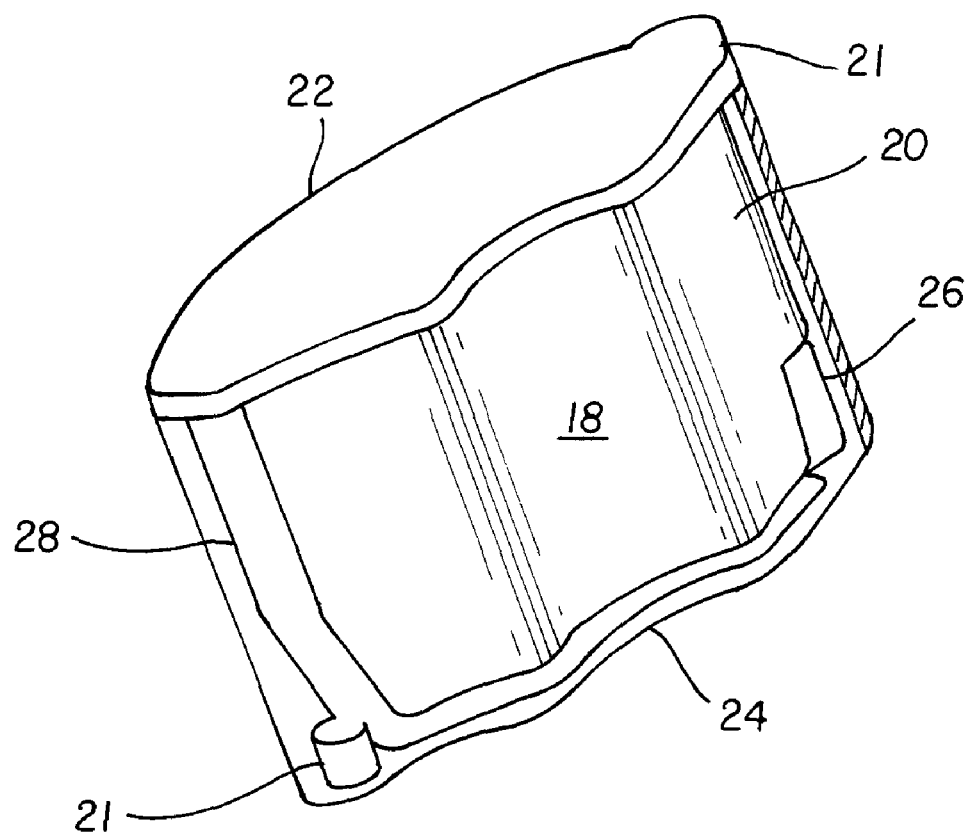
FIG. 2 is an illustrating of a hydrogen peroxide submunition utilized in the system illustrated in FIG. 1.

FIG. 2 is a cutaway view of an example of a hydrogen peroxide submunition 18 in accordance with a preferred embodiment of the invention. The hydrogen peroxide submunition 18 includes a fluoropolymer (Teflon™) bladder 20 located in a casing 22 (casing 22 is shown with the top in place and the side cut away in the illustration). The bladder 20 includes two thinned sections containing a hot wire molded therein to weaken the bladder 20 for rupture when a fuse 26 is activated. The thinned sections are spatially aligned with nozzle inlets 21 provided for single use rupture valves. The bladder 20 is pressurized by an electrically ignited sodium azide charge 24 located between the bladder 20 and the casing 22. The charge 24 is preferably implemented in the form of an air bag structure that expands to apply pressure to the bladder 20. Once the bladder 20 is ruptured, the hydrogen peroxide flows through a baffle 28 and out of the nozzle inlets 21 to dispersion nozzles (not shown) that vaporize the hydrogen peroxide. A nozzle/disseminator, produced by Pratt & Whitney under license from the Steris Corp., has been found to provide suitable small, uniform droplets (<2.5 µm) with a projection distance >30 m, and can also be tuned for optimal spray patterns.

The mobile launch platform 10 is preferably implemented using the Lockheed Martin Multiple Launch Rocket System M270A1 (MLRS). In the embodiment illustrated embodiment shown in FIG. 1, the mobile launch platform 10 is preferably positioned outside a protected area in a location that will allow total coverage of the protected area. Guided M30 MLRS (GMLRS) missiles launched from the MLRS are preferably utilized for the rockets 12 for scenarios that require a large area/massive response located ≧10 km away from the protected area. The GMLRS is an all weather, precision-guided rocket with a 196 pound payload capacity. Its modular design can be easily adapted for delivering the hydrogen peroxide submunitions and explosive submunitions required by the present system.

The explosives provided in the explosive submunitions are detonated in succession and superimposed in space to create the required ultraviolet radiation. Specifically, the ultraviolet radiation splits the hydrogen peroxide into two OH radicals (.OH) that rapidly decontaminate the chemical and/or biological agents contained in the cloud 14. The amount of hydrogen peroxide and explosives required varies depending on the size of the cloud 14 and concentration of agents within the cloud 14. It is estimated, however, that one ton of agent spread over an area of $10^5$ cubic meters can be neutralized using 0.5 tons of explosives and 0.25 tons of hydrogen peroxide. The hydrogen peroxide is preferably dispersed first for chemical agents, because the primary kill mechanism for chemical agents is the OH radical reaction. The dispersal order is preferably reversed for the biological agents, as the primary rapid kill mechanism for the biological agents is the ultraviolet radiation.

The optimal time for classification/identification (CI) of the agent within the cloud and application of an effective countermeasure (CM), namely the launch of the rockets 12 (hereinafter referred to as "CM rockets 12") containing hydrogen peroxide submunitions and explosive submunitions from the mobile launch platform 10, is at the time of the initial formation of the cloud 14 or shortly thereafter. It is at the point of formation that the cloud 14 is most concentrated and can most easily be evaluated and decontaminated. Accordingly, the system also preferably includes a CI mechanism for quickly identifying if the cloud 14 is in fact a threat, identifying the chemical and/or biological agents within the cloud 14 if it is a threat, and the concentrations of the chemical and/or biological agents.

In a preferred embodiment of the system as shown in FIG. 1, the CI mechanism includes one or more Micro Air Vehicles (MAV) 30 carrying chemical and biological agent sensors that can be launched into the cloud 14 on one or more MAV rockets 32. The MAV rockets 32 are preferably launched from a MAV mobile launcher 34 positioned within the protected area. The MAV mobile launcher 34 can be used to provide responsive surface-to-air type CI coverage to a range of about 10 km. In addition, in response to close threats, the MAV mobile launcher 34 can also be used to launch the CM rockets 12 as well as the MAV rockets 32. The MAV mobile launcher 34 is preferably implemented using two U.S. Army Lightweight M260 or M261 type Launchers to deliver MAV rockets 32 based on a two conventional 70-mm rocket variants. Preferably, a Skyfire 70-10M rocket is used in long range for scenarios (greater than 3 km from the protected area perimeter), while a tailored Hydra-70 rocket is used for short range scenarios (less than 3 km from the protected area perimeter). The Hydra-70 rockets preferably include integral descent decelerators to minimize collateral damage for overhead scenarios, namely, when the cloud is close to or directly overhead of the protected area.

The flying of a sensor directly into the cloud 14 via the MAV 30 provides the advantages of sensitivity, selectivity, and speed of detection. Since the sensors will be in direct contact with the agents, they can provide the most accurate method of detection and will not suffer from line of sight deployment issues. The sensors employed are preferably effective in differentiating between chemical and biological agents, as well as differentiating between individual chemical agents, thereby allowing the command center 16 us to deploy an appropriate amount of CM rockets 12 into the cloud 14 to neutralize any detected threat. There are currently many types of chemical and biological sensors available that can be employed by the present system including, for example, the JUNO™ chemical detector developed by Sionex Corporation and the TAC-BIO sensor developed by the U.S. Army Edgewood Chemical Biological Center (ECBC). The type of detectors employed will necessarily depend on the type of threat scenario envisioned. The MAV mobile launcher 34 can easily be loaded with MAVs 30 having sensors with different capabilities if so desired.

The total amount of CM delivered is determined to optimize the kill effectiveness with the least logistics and cost associated with the deployment of the system. For a large scenario with 1000 kg (2200 lbs) of agent involved, the total amount of CM required is, at most, projected to be 1100 kg. This represents a nearly 1:1 ratio of CM to agent to defeat the largest concentration of threat agents.

The basic operation of the system will now be described in response to the detection of a suspected cloud of chemical and/or biological agent. Upon notification of detection, for example by a light detection and ranging system (LIDAR) not shown, the command center 16 initiates launch of a MAV rocket 32 by sending a launch command to the MAV mobile launcher 34 via a communication network (not shown). Depending on the range of the potential threat, the MAV rocket 32 selected for launch will either by a Hydra-70 rocket or a Skyfire 70-10M rocket in the illustrated example. In response to the launch command, the MAV mobile launcher 34 launches one or more MAV rockets 32 into the suspect cloud. The MAVs 30 contained within the MAV rockets 32 detach from the MAV rockets 32 and activate their integrated sensors to detect whether a chemical and/or biological agent is present within the cloud 14. Data from the MAVs 26 is transmitted back to the command center 16 via the communication network indicating the presence or absence of a chemical and/or biological agent.

If an agent is detected, the command center 16 calculates the amount and order (explosives first for biological agents and second for chemical agents; peroxide first for chemical agents and second for biological agents) of delivery of CM rockets 12 to be launched from the mobile launch platform 10, based on the identification of the agent provided by the data sent back by the MAVs 30. The command center 16 then sends a launch command to the mobile launch platform 10 to launch the correct number and sequence of CM rockets 12. The mobile launch platform 10 proceeds to launch the CM rockets 12 in response to the launch command received from the command center 16. The CM rockets 12 enter the agent cloud and the hydrogen peroxide submunitions 18 and explosive submunitions 36 are subsequently dispersed within the agent cloud 14 in the appropriate sequence. The hydrogen peroxide submunitions 18 dispense vaporized hydrogen peroxide and the explosive submunitions 36 are detonated in accordance with a predetermined detonation pattern. Once the initial CM response has been completed by the dispersion of the vaporized hydrogen peroxide and the detonation of the explosives, the command center 16 can order the launch of additional MAVs 30 to check and see if the decontamination of the agent cloud 14 has been successful. If any chemical or biological agents remain, as the command center 16 can order a second round of CM.

The effectiveness of the system depends on the ability to efficiently generate ultraviolet radiation at sufficient levels to cause the hydrogen peroxide to break down into the radical elements. Ultraviolet photons are generated by implanting numerous exploding point sources, i.e. the explosives of the explosive submunitions, throughout the threat cloud as described above. The point sources are preferably distributed with a separation of approximately 10 m between centers. The rationale for such a separation scale is dictated by the mean free path of the photons that are effective in destroying the hazardous agent within the cloud.

Each ultraviolet radiation generator, i.e. the explosive submunitions, preferably contain four explosive charges totaling approximately 3 kg and consisting of two 0.5 kg subunits and two 1.0 kg subunits. In each kill domain, the grouped explosives are ignited sequentially with a time delay of preferably about 500 µs between detonations. During this delay, the shock formed by the explosive subunit will accelerate proximal material (air) away from the explosion site rarefying the local environment. The first explosive interacts with the air ($O_2$, $N_2$) while subsequent explosions accelerate the gaseous detonation products of the previous explosions from the blast center. If highly energetic explosives (7-14 MJ/kg) are employed, after two sequenced explosions of ½ kg each, a reduction of density from STP is observed. An air density of $10^{-4}$ g/cc is achieved within a sphere of radius of about 2 m. The hole formed provides a large spherical surface created at the interface between the high and low pressure regions, from which ultraviolet radiation emanates. The explosive ejecta flows radially outwards at a velocity of nearly 7 km/s, while the material from the shell boundary reverses and flows inward at 1 to 2 km/s. The collision of these flows forms a high temperature domain that radiates $\sim 10^4$K. The air at the boundary of the shell has a density of $\sim 3 \times 10^{-4}$ g/cc in which the mean free path of a photon of 200 nm is only a few cm. Therefore, a spherical black body radiating source forms at a distance of 1.5-2 m radius. It is to be noted that if the entire explosive energy had been delivered at once, without generating the initial hole, one would obtain an extremely small radius for the radiating source of only a few 10's of cm, and thus the radiation intensity would have been an order of magnitude less.

Figure 3A:
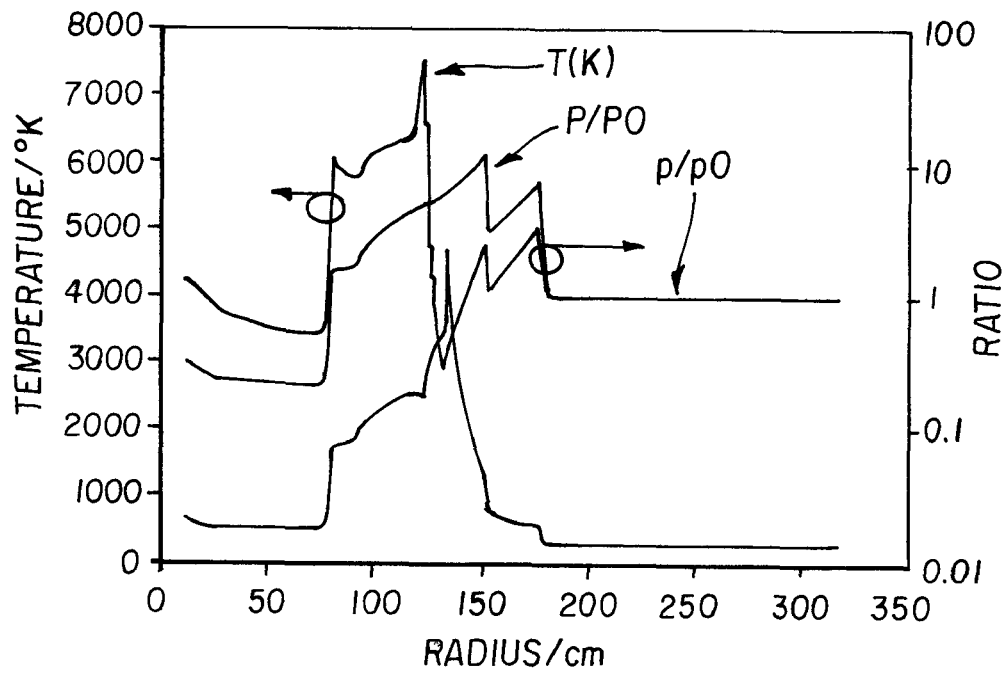
FIGS. 3A and 3B are graphs illustrating temperature, pressure, and density due to a sequence of explosions employed by the system illustrated in FIG. 1.
Figure 3B:
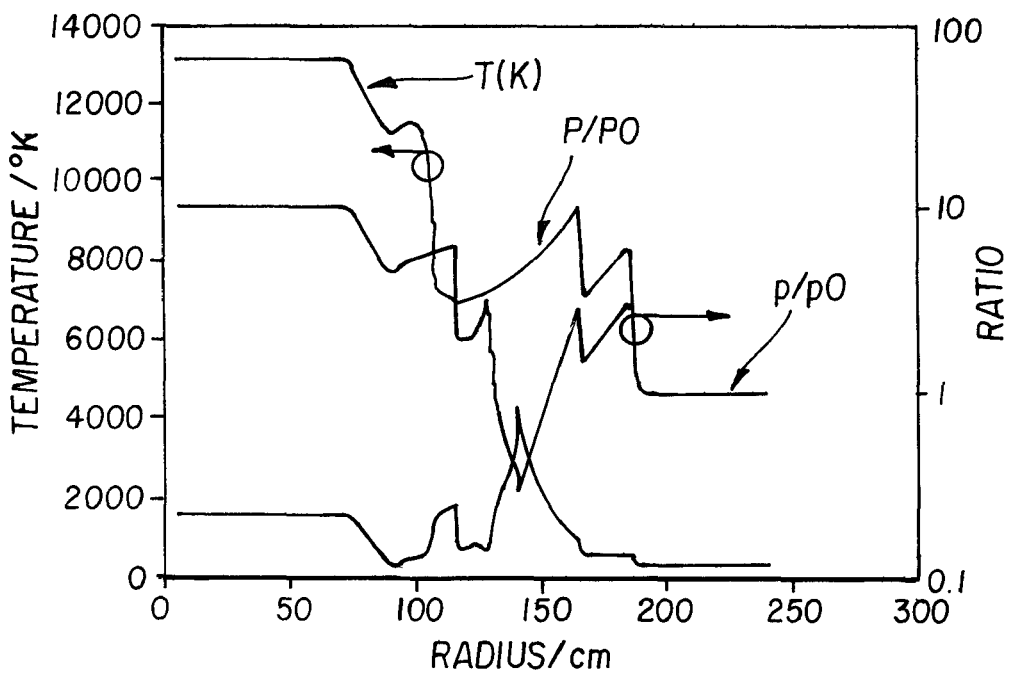

Extensive spherically symmetric 1D simulations to model both the temperature profiles and ultraviolet radiation from the explosions just described have shown that approximately 30% of the explosive energy goes directly into ultraviolet radiation generation. In addition, temperatures of $10^4$ K and ultraviolet flux of approximately 6 J/cm$^2$ is generated at radius of 5 m. In this case, Naval hydrodynamics code GEMINI was used to simulate the explosion without radiation as a first order approximation to understand the temperatures created. A radiation hydrodynamics code, SPHERAD, was then employed to estimate the radiative output and account for energy losses due to the radiation. FIGS. 3A and 3B show the temperature, pressure, and density due to a sequence of explosions of 7, 7, and 14 MJ with a sequencing time of 0.5 ms. In FIG. 3A, the aftermath of a single charge is shown after 0.498 ms, where the hole diameter is approximately 80 cm. FIG. 3B shows the temperature and densities 0.1 ms after the $3^{rd}$ explosion, the temperature reaches approximately 13000 K in the core due to radiative heating. The effect of the density hole is seen by the dramatic rise in temperature of the explosive.

In addition to modeling ultraviolet radiation generation as described above, modeling of chemical and biological kill factors based on the resultant calculated radiation have also been performed for various agents and threat scenarios. The modeling was done assuming a 3 m radius fireball generated from the explosives. Given these parameters, the required energy for complete remediation with ultraviolet radiation activated hydrogen peroxide requires a sum-total energy release within the cloud (with peroxide concentration ratios being chosen such that initial concentrations of hydrogen peroxide were 1.5 and 3 times the initial agent concentrations) to be approximately 3.43 GJ.

All energy at wavelengths from 100 to 200 nm is initially absorbed by oxygen and then reemitted into the column at wavelengths longer than 200 nm. The energy >350 nm does not contribute as the absorption cross-section is negligible. The energy contributing the most to the remediation is between 200-350 nm. In this bounded calculation, it is assumed that all emitters can be treated like a black-body ($10^4$ K black body, 2 msec duration). In this case it was found that 30% of the last two subcharges provide remediation. Similar energies are obtained from total agent quantities using energy-mass balance calculations. These first order calculations do not include any remediation contribution from direct photolysis and therefore underestimate the amount of agents destroyed by up to 10%.

For biological agents, the kill mechanism is direct photolysis. It is a threshold process due to the requirement of exceeding the natural DNA repair capacity of the organism. The literature photon flux value required for direct photolysis varies between 25 to 100 mJ/cm$^2$. Because of the overall geometry of deployment for the ultraviolet generators, as described above, a value of 6 J/cm$^2$ is created for any point between the close packed radiating shells. With multi source illumination, there is enough photon flux for direct photolytic mechanisms within a total radius of 7 to 10 m. As both the concentration of agent and the kill thresholds are low, high photon fluxes remain throughout this region.

Based on the modeling performed, the CM ratio—depending on the agent to be neutralized—should preferably be in a range of 0.5-1 peroxide to agent. Further, using a 0.5-1 peroxide to agent ratio allows the use of explosives with energies of 7 MJ/kg, which is a readily achievable energy load with conventional explosives such as PTX. Thus, the system can be readily implemented utilizing conventional explosive and missile technology.

Although the use of peroxide by itself or ultraviolet radiation by itself is known, the use of peroxide alone requires decontamination periods measured in hours and days while the sue of ultraviolet radiation alone can only be used to destroy biological agents. The present system and method combines the use of both peroxide and ultraviolet radiation to decontaminate both chemical and biological agent threats, and further employs ultraviolet radiation produced from the detonation of the explosive submunitions to break up the peroxide into OH radicals that further act as decontamination agents. The present system and method provides flexibility in addressing a variety of threat scenarios while being able to provide rapid decontamination in a matter of seconds and minutes as opposed to hours and days using conventional processes.

The invention has been described with reference to certain preferred embodiments thereof. It will be understood, however, that modifications and variations are possible within the scope of the appended claims. For example, in the event of smaller persistent threats, for example a situation in which a small amount of agent is dispensed over several minutes and the amount of corresponding CM is small, the MAVs may themselves be modified to disperse hydrogen peroxide within the cloud instead of requiring a separate CM rocket. Still further, depending on the type of threat presented, the launching of the MAV rockets and the CM rockets can be performed by one launcher instead of two launchers as shown in the illustrated embodiment. Still further, the various concentration levels, energy requirements, explosive charges will necessarily vary depending on the type of treat scenario and agent employed.

What is claimed is:

1. A method of decontamination of an agent cloud comprising:
    dispersing hydrogen peroxide within the agent cloud; and
    generating sufficient ultraviolet radiation within the agent cloud with an explosive charge which is detonated within the cloud to cause at least a portion of the hydrogen peroxide to break up into radical species.

2. A method of decontamination of an agent cloud as claimed in claim 1, wherein multiple explosive charges are detonated within the agent cloud in a predefined sequence to generate ultraviolet radiation.

3. A method of decontamination of an agent cloud as claimed in claim 2, wherein multiple explosive charges are detonated within the agent cloud.

4. A method of decontamination of an agent cloud as claimed in claim 3, wherein the multiple explosive charges total about 3 kg.

5. A method of decontamination of an agent cloud as claimed in claim 4, wherein the multiple explosive charges include two 0.5 kg subunits and two 1.0 kg subunits.

6. A method of decontamination of an agent cloud as claimed in claim 3, wherein the multiple explosive charges are ignited sequentially with a time delay of about 500 μs between detonations.

7. A method of decontamination of an agent cloud as claimed in claim 2, wherein the detonation of the explosive charges generates ultraviolet flux of about 6 J/cm$^2$ at a radius of 5 m.

8. A method of decontamination of an agent cloud as claimed in claim 1, wherein the ultraviolet radiation is in a range of 200-250 nm.

9. A method of decontamination of an agent cloud as claimed in claim 1, wherein the agent cloud includes chemical or biological agents, and the radical species are sufficient to neutralize the agents within the cloud.

10. A method of decontamination of an agent cloud as claimed in claim 1, wherein a ratio of hydrogen peroxide to agent within the cloud is between 0.5-1.0.

11. A system for decontamination of an agent cloud comprising:
    a mechanism that disperses hydrogen peroxide within the agent cloud; and
    a mechanism that generates sufficient ultraviolet radiation within the agent cloud to cause at least a portion of the hydrogen peroxide to break up into radical species, the mechanism comprising multiple explosive charges which are detonated within the cloud, wherein the multiple explosive charges total about 3 kg.

12. A system for decontamination of an agent cloud as claimed in claim 11, wherein the multiple explosive charges include two 0.5 kg subunits and two 1.0 kg subunits.

13. A system for decontamination of an agent cloud comprising:
    a mechanism that disperses hydrogen peroxide within the agent cloud; and
    a mechanism that generates sufficient ultraviolet radiation within the agent cloud to cause at least a portion of the hydrogen peroxide to break up into radical species, the mechanism comprising multiple explosive charges which are detonated within the cloud, wherein the multiple explosive charges are ignited sequentially with a time delay of approximately 500 μs between detonations.

14. A system for decontamination of an agent cloud comprising:

a mechanism that disperses hydrogen peroxide within the agent cloud; and a mechanism that generates sufficient ultraviolet radiation within the agent cloud to cause at least a portion of the hydrogen peroxide to break up into radical species, the mechanism comprising multiple explosive charges which are detonated within the cloud, wherein the multiple explosive charges are detonated in a predefined sequence and wherein the detonation of the explosive charges generates ultraviolet flux of approximately 6 $J/cm^2$ at a radius of 5 m.

15. A system for decontamination of an agent cloud as claimed in claim 14, wherein the ultraviolet radiation is in a range of 200-250 nm.

16. A system for decontamination of an agent cloud as claimed in claim 14, wherein the agent cloud includes chemical or biological agents, and the radical species are sufficient to neutralize the agents within the cloud.

17. A system for decontamination of an agent cloud as claimed in claim 14, wherein a ratio of hydrogen peroxide to agent within the cloud is between 0.5-1.0.

18. A system for decontamination of an agent cloud as claimed in claim 14, additionally comprising a mechanism for identifying chemical or biological agents within the cloud.

\* \* \* \* \*